(12) United States Patent
Nock et al.

(10) Patent No.: US 6,686,154 B2
(45) Date of Patent: Feb. 3, 2004

(54) SCREENING OF PHAGE DISPLAYED PEPTIDES WITHOUT CLEARING OF THE CELL CULTURE

(75) Inventors: Steffen Nock, Redwood City, CA (US); Paul D. Kassner, San Mateo, CA (US)

(73) Assignee: Zyomyx, Inc., Hayward, CA (US)

( * ) Notice: Subject to any disclaimer, the term of this patent is extended or adjusted under 35 U.S.C. 154(b) by 0 days.

(21) Appl. No.: 09/874,547

(22) Filed: Jun. 4, 2001

(65) Prior Publication Data

US 2002/0058269 A1 May 16, 2002

Related U.S. Application Data

(60) Provisional application No. 60/209,503, filed on Jun. 5, 2000.

(51) Int. Cl.[7] .............................................. C12Q 1/68
(52) U.S. Cl. ............................. 435/6; 435/5; 435/7.1; 435/235.1; 435/320.1
(58) Field of Search ......................... 435/7.1, 5, 7.32, 435/DIG. 4, DIG. 8, DIG. 24, DIG. 47, 6; 424/130.1 T, 142.1; 530/387.1 T

(56) References Cited

U.S. PATENT DOCUMENTS 6,451,527 B1 * 9/2002 Larocca et al. ................. 435/6

FOREIGN PATENT DOCUMENTS

| WO | WO 95/16027 A1 | 6/1995 |
| WO | WO 95/34648 A1 | 12/1995 |
| WO | WO 00/31246 A2 | 6/2000 |

OTHER PUBLICATIONS

Cabilly, S.; Heldman, J.; Katchalski–Katzir, E. "Screening Phage Display Peptide Libraries on Nitrocellulose Membranes" In: Combinatorial Peptide Library Protocols. Edited by S. Cabilly Totowa, New Jersey: Humana Press, 1998.*
Smith, G. P.; Scott, J. K. "Libraries of Peptides and Proteins Displayed on Filamentous Phage" In: Methods in Enzymology vol. 217. Edited by R. Wu. New York, Academic Press, Inc. 1993.*
Light, J.; Maki, R.; Assa–Munt, N. "Expression cloning of cDNA by phage display selection" Nucleic Acids Research, 1996, 24(21), 4367–4368.*
WO 99/57312 (Cahill et al) Nov. 11, 1999.*
Griffiths, et al. "Isolation of High Affinity Human Antibodies Directly From Large Synthetic Repertoires" *Embo Journal* (Jul. 1994) Vo. 13(14), pp. 3245–3260.
Haard, et al. "A Large Non–immunized Human Fab Fragment Phage Library That Permits Rapid Isolation and Kinetic Analysis of High Affity Antibodies" *J. of Biological Chemistry* (Jun. 1999) vol. 274(26), pp. 18218–18230.
Krebber, te al. "Selectivity–infective Phage (SIP): A Mechanistic Dissection of a Novel in vivio Selection for Protein–ligand Interactions" *J. Molecular Biology* (1997) vol. 268(3), pp. 607–618.
Phillps, Lisa M., "Detection of Antibody Display Phage Without Clearing of Bacterial Culture" *Biotechniques* (2000) vol. 26(4), pp. 737–740.
Sheets, et al., "Efficient Construction of a Large Nonimmune Phage Antibody Library: The Production of High–affinity Human Single–chain Antibodies to Protein Antibodies to Protein Antigen" *Proc. Natl. Acad. Sci.* (May 1998) vol. (95), pp. 6157–6162.

* cited by examiner

*Primary Examiner*—Bennett Celsa
*Assistant Examiner*—Jon D. Epperson
(74) *Attorney, Agent, or Firm*—Townsend and Townsend and Crew LLP

(57) ABSTRACT

This invention provides methods for screening populations of phage-displayed polypeptides that are particularly well-suited for high-throughput screening. The methods do not require the clearing of cells from a culture used to obtain the population of phage or other replicable genetic packages. Accordingly, the invention provides methods for forming complexes between a replicable genetic package displaying a polypeptide fusion and a target molecule in an uncleared cell culture containing replicable genetic package. Compositions made up of an uncleared cell culture containing replicable genetic packages displaying a polypeptide fusion and a target molecule are provided in the invention as well.

19 Claims, 2 Drawing Sheets

SEQUENCE LISTING

<160> NUMBER OF SEQ ID NOS: 84

<210> SEQ ID NO 1
<211> LENGTH: 48
<212> TYPE: DNA
<213> ORGANISM: Artificial Sequence
<220> FEATURE:
<223> OTHER INFORMATION: Primers for ScFv and Fab library generation
      (Table I)- MCH1G1R

<400> SEQUENCE: 1
attggcgcgc cttattaaca atccctgggc acaattttct tgtccacc                48

<210> SEQ ID NO 2
<211> LENGTH: 44
<212> TYPE: DNA
<213> ORGANISM: Artificial Sequence
<220> FEATURE:
<223> OTHER INFORMATION: Primers for ScFv and Fab library generation
      (Table I)- MCH1-G2A

<400> SEQUENCE: 2
attggcgcgc cttattaaca gggcttgatt gtgggccctc tggg                    44

<210> SEQ ID NO 3
<211> LENGTH: 45
<212> TYPE: DNA
<213> ORGANISM: Artificial Sequence
<220> FEATURE:
<223> OTHER INFORMATION: Primers for ScFv and Fab library generation
      (Table I)-MCH1-G2B

<400> SEQUENCE: 3
attggcgcgc cttattaaca ggggttgatt gttgaaatgg gcccg                   45

<210> SEQ ID NO 4
<211> LENGTH: 50
<212> TYPE: DNA
<213> ORGANISM: Artificial Sequence
<220> FEATURE:
<223> OTHER INFORMATION: Primers for ScFv and Fab library generation
      (Table I)- MHV-Back2

<400> SEQUENCE: 4
ttattactcg cggcccagcc ggccatggcc gatgtgaagc ttcaggagtc              50

<210> SEQ ID NO 5
<211> LENGTH: 50
<212> TYPE: DNA

```
<213> ORGANISM: Artificial Sequence
<220> FEATURE:
<223> OTHER INFORMATION: Primers for ScFv and Fab library generation
      (Table I)- MHC-Back2

<400> SEQUENCE: 5
ttattactcg cggcccagcc ggccatggcc caggtgcagc tgaaggagtc            50

<210> SEQ ID NO 6
<211> LENGTH: 50
<212> TYPE: DNA
<213> ORGANISM: Artificial Sequence
<220> FEATURE:
<223> OTHER INFORMATION: Primers for ScFv and Fab library generation
      (Table I)- MHC-Back3

<400> SEQUENCE: 6
ttattactcg cggcccagcc ggccatggcc caggtgcagc tgaagcagtc            50

<210> SEQ ID NO 7
<211> LENGTH: 50
<212> TYPE: DNA
<213> ORGANISM: Artificial Sequence
<220> FEATURE:
<223> OTHER INFORMATION: Primers for ScFv and Fab library generation
      (Table I)- MHV-Back4

<400> SEQUENCE: 7
ttattactcg cggcccagcc ggccatggcc caggttactc tgaaagagtc            50

<210> SEQ ID NO 8
<211> LENGTH: 51
<212> TYPE: DNA
<213> ORGANISM: Artificial Sequence
<220> FEATURE:
<223> OTHER INFORMATION: Primers for ScFv and Fab library generation
      (Table I)- MHV-Back5

<400> SEQUENCE: 8
ttattactcg cggcccagcc ggccatggcc gaggtccagc tgcaacaatc t          51

<210> SEQ ID NO 9
<211> LENGTH: 50
<212> TYPE: DNA
<213> ORGANISM: Artificial Sequence
<220> FEATURE:
<223> OTHER INFORMATION: Primers for ScFv and Fab library generation
      (Table I)- MHV-Back6

<400> SEQUENCE: 9
ttattactcg cggcccagcc ggccatggcc gaggtccagc tgcagcagtc            50

<210> SEQ ID NO 10
<211> LENGTH: 51
<212> TYPE: DNA
<213> ORGANISM: Artificial Sequence
<220> FEATURE:
<223> OTHER INFORMATION: Primers for ScFv and Fab library generation
      (Table I)- MHV-Back7

<400> SEQUENCE: 10
ttattactcg cggcccagcc ggccatggcc caggtccaac tgcagcagcc t          51

<210> SEQ ID NO 11
<211> LENGTH: 50
<212> TYPE: DNA
<213> ORGANISM: Artificial Sequence
```

<220> FEATURE:
<223> OTHER INFORMATION: Primers for ScFv and Fab library generation
       (Table I)- MHV-Back8

<400> SEQUENCE: 11
ttattactcg cggcccagcc ggccatggcc gaggtgaagc tggtggagtc         50

<210> SEQ ID NO 12
<211> LENGTH: 50
<212> TYPE: DNA
<213> ORGANISM: Artificial Sequence
<220> FEATURE:
<223> OTHER INFORMATION: Primers for ScFv and Fab library generation
       (Table I)- MHV-Back9

<400> SEQUENCE: 12
ttattactcg cggcccagcc ggccatggcc gaggtgaagc tggtggaatc         50

<210> SEQ ID NO 13
<211> LENGTH: 50
<212> TYPE: DNA
<213> ORGANISM: Artificial Sequence
<220> FEATURE:
<223> OTHER INFORMATION: Primers for ScFv and Fab library generation
       (Table I)- MHV-Back10

<400> SEQUENCE: 13
ttattactcg cggcccagcc ggccatggcc gatgtgaact tggaagtgtc         50

<210> SEQ ID NO 14
<211> LENGTH: 33
<212> TYPE: DNA
<213> ORGANISM: Artificial Sequence
<220> FEATURE:
<223> OTHER INFORMATION: Primers for ScFv and Fab library generation
       (Table I)- MHV-For1

<400> SEQUENCE: 14
acctggcgcg cctgcagaga cagtgaccag agt                           33

<210> SEQ ID NO 15
<211> LENGTH: 42
<212> TYPE: DNA
<213> ORGANISM: Artificial Sequence
<220> FEATURE:
<223> OTHER INFORMATION: Primers for ScFv and Fab library generation
       (Table I)- MHV-For1b

<400> SEQUENCE: 15
accgcctcca cctggcgcgc ctgcagagac agtgaccaga gt                 42

<210> SEQ ID NO 16
<211> LENGTH: 33
<212> TYPE: DNA
<213> ORGANISM: Artificial Sequence
<220> FEATURE:
<223> OTHER INFORMATION: Primers for ScFv and Fab library generation
       (Table I)- MHV-For2

<400> SEQUENCE: 16
acctggcgcg cctgaggaga ctgtgagagt ggt                           33

<210> SEQ ID NO 17
<211> LENGTH: 42
<212> TYPE: DNA
<213> ORGANISM: Artificial Sequence
<220> FEATURE:

```
<223> OTHER INFORMATION: Primers for ScFv and Fab library generation
      (Table I)- MHV-for2b

<400> SEQUENCE: 17
accgcctcca cctggcgcgc ctgaggagac tgtgagagtg gt                    42

<210> SEQ ID NO 18
<211> LENGTH: 33
<212> TYPE: DNA
<213> ORGANISM: Artificial Sequence
<220> FEATURE:
<223> OTHER INFORMATION: Primers for ScFv and Fab library generation
      (Table I)- MHV-For3

<400> SEQUENCE: 18
acctggcgcg cctgaggaga cggtgactga ggt                             33

<210> SEQ ID NO 19
<211> LENGTH: 42
<212> TYPE: DNA
<213> ORGANISM: Artificial Sequence
<220> FEATURE:
<223> OTHER INFORMATION: Primers for ScFv and Fab library generation
      (Table I)- MHV-for3b

<400> SEQUENCE: 19
accgcctcca cctggcgcgc ctgaggagac ggtgactgag gt                   42

<210> SEQ ID NO 20
<211> LENGTH: 33
<212> TYPE: DNA
<213> ORGANISM: Artificial Sequence
<220> FEATURE:
<223> OTHER INFORMATION: Primers for ScFv and Fab library generation
      (Table I)- MHV-For4

<400> SEQUENCE: 20
acctggcgcg cctgaggaga cggtgaccgt ggt                             33

<210> SEQ ID NO 21
<211> LENGTH: 42
<212> TYPE: DNA
<213> ORGANISM: Artificial Sequence
<220> FEATURE:
<223> OTHER INFORMATION: Primers for ScFv and Fab library generation
      (Table I)- MHV-for4b

<400> SEQUENCE: 21
accgcctcca cctggcgcgc ctgaggagac ggtgaccgtg gt                   42

<210> SEQ ID NO 22
<211> LENGTH: 39
<212> TYPE: DNA
<213> ORGANISM: Artificial Sequence
<220> FEATURE:
<223> OTHER INFORMATION: Primers for ScFv and Fab library generation
      (Table I)- MKV-back1

<400> SEQUENCE: 22
tctggcggtg gcggatcgga tgttttgatg acccaaact                       39

<210> SEQ ID NO 23
<211> LENGTH: 39
<212> TYPE: DNA
<213> ORGANISM: Artificial Sequence
<220> FEATURE:
```

<223> OTHER INFORMATION: Primers for ScFv and Fab library generation
      (Table I)- MKV-Back2

<400> SEQUENCE: 23
tctggcggtg gcggatcgga tattgtgatg acgcaggct        39

<210> SEQ ID NO 24
<211> LENGTH: 36
<212> TYPE: DNA
<213> ORGANISM: Artificial Sequence
<220> FEATURE:
<223> OTHER INFORMATION: Primers for ScFv and Fab library generation
      (Table I)- MKV-Back3

<400> SEQUENCE: 24
tctggcggtg gcggatcgga tattgtgata acccag           36

<210> SEQ ID NO 25
<211> LENGTH: 39
<212> TYPE: DNA
<213> ORGANISM: Artificial Sequence
<220> FEATURE:
<223> OTHER INFORMATION: Primers for ScFv and Fab library generation
      (Table I)- MKV-Back4

<400> SEQUENCE: 25
tctggcggtg gcggatcgga cattgtgctg acccaatct        39

<210> SEQ ID NO 26
<211> LENGTH: 39
<212> TYPE: DNA
<213> ORGANISM: Artificial Sequence
<220> FEATURE:
<223> OTHER INFORMATION: Primers for ScFv and Fab library generation
      (Table I)- MKV-Back5

<400> SEQUENCE: 26
tctggcggtg gcggatcgga cattgtgatg acccagtct        39

<210> SEQ ID NO 27
<211> LENGTH: 39
<212> TYPE: DNA
<213> ORGANISM: Artificial Sequence
<220> FEATURE:
<223> OTHER INFORMATION: Primers for ScFv and Fab library generation
      (Table I)- MKV-Back6

<400> SEQUENCE: 27
tctggcggtg gcggatcgga tattgtgcta actcagtct        39

<210> SEQ ID NO 28
<211> LENGTH: 39
<212> TYPE: DNA
<213> ORGANISM: Artificial Sequence
<220> FEATURE:
<223> OTHER INFORMATION: Primers for ScFv and Fab library generation
      (Table I)- MKV-Back7

<400> SEQUENCE: 28
tctggcggtg gcggatcgga tatccagatg acacagact        39

<210> SEQ ID NO 29
<211> LENGTH: 39
<212> TYPE: DNA
<213> ORGANISM: Artificial Sequence
<220> FEATURE:

```
<223> OTHER INFORMATION: Primers for ScFv and Fab library generation
      (Table I)- MKV-Back8

<400> SEQUENCE: 29
tctggcggtg gcggatcgga catccagctg actcagtct                    39

<210> SEQ ID NO 30
<211> LENGTH: 39
<212> TYPE: DNA
<213> ORGANISM: Artificial Sequence
<220> FEATURE:
<223> OTHER INFORMATION: Primers for ScFv and Fab library generation
      (Table I)- MKV-Back9

<400> SEQUENCE: 30
tctggcggtg gcggatcgca aattgttctc acccagtct                    39

<210> SEQ ID NO 31
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MKV-For1

<400> SEQUENCE: 31
gatggtgatg tgcggccgcc cgtttcagct ccagcttg                     38

<210> SEQ ID NO 32
<211> LENGTH: 40
<212> TYPE: DNA
<213> ORGANISM: Artificial Sequence
<220> FEATURE:
<223> OTHER INFORMATION: Primers for ScFv and Fab library generation
      (Table I)- MKV-For2

<400> SEQUENCE: 32
gatggtgatg tgcggccgcc cgttttattt ccagcttggt                   40

<210> SEQ ID NO 33
<211> LENGTH: 39
<212> TYPE: DNA
<213> ORGANISM: Artificial Sequence
<220> FEATURE:
<223> OTHER INFORMATION: Primers for ScFv and Fab library generation
      (Table I)- MKV-For3

<400> SEQUENCE: 33
gatggtgatg tgcggccgcc cgttttattt ccaactttg                    39

<210> SEQ ID NO 34
<211> LENGTH: 40
<212> TYPE: DNA
<213> ORGANISM: Artificial Sequence
<220> FEATURE:
<223> OTHER INFORMATION: Primers for ScFv and Fab library generation
      (Table I)-MKV-For4

<400> SEQUENCE: 34
gatggtgatg tgcggccgcg gatacagttg gtgcagcatc                   40

<210> SEQ ID NO 35
<211> LENGTH: 55
<212> TYPE: DNA
<213> ORGANISM: Artificial Sequence
<220> FEATURE:
```

<223> OTHER INFORMATION: Primers for ScFv and Fab library generation
      (Table I)- MVH1

<400> SEQUENCE: 35
cctttctatg cggcccagcc ggccatggcc gaggtrmagc ttcaggagtc aggac     55

<210> SEQ ID NO 36
<211> LENGTH: 55
<212> TYPE: DNA
<213> ORGANISM: Artificial Sequence
<220> FEATURE:
<223> OTHER INFORMATION: Primers for ScFv and Fab library generation
      (Table I)- MVH2

<400> SEQUENCE: 36
cctttctatg cggcccagcc ggccatggcc gaggtscagc tkcagcagtc aggac     55

<210> SEQ ID NO 37
<211> LENGTH: 53
<212> TYPE: DNA
<213> ORGANISM: Artificial Sequence
<220> FEATURE:
<223> OTHER INFORMATION: Primers for ScFv and Fab library generation
      (Table I)- MVH3

<400> SEQUENCE: 37
cctttctatg cggcccagcc ggccatggcc caggtgcagc tgaagsastc agg       53

<210> SEQ ID NO 38
<211> LENGTH: 55
<212> TYPE: DNA
<213> ORGANISM: Artificial Sequence
<220> FEATURE:
<223> OTHER INFORMATION: Primers for ScFv and Fab library generation
      (Table I)- MVH4

<400> SEQUENCE: 38
cctttctatg cggcccagcc ggccatggcc gaggtgcagc ttcaggagtc sggac     55

<210> SEQ ID NO 39
<211> LENGTH: 55
<212> TYPE: DNA
<213> ORGANISM: Artificial Sequence
<220> FEATURE:
<223> OTHER INFORMATION: Primers for ScFv and Fab library generation
      (Table I)- MVH5

<400> SEQUENCE: 39
cctttctatg cggcccagcc ggccatggcc gargtccagc tgcaacagtc yggac     55

<210> SEQ ID NO 40
<211> LENGTH: 53
<212> TYPE: DNA
<213> ORGANISM: Artificial Sequence
<220> FEATURE:
<223> OTHER INFORMATION: Primers for ScFv and Fab library generation
      (Table I)- MVH6

<400> SEQUENCE: 40
cctttctatg cggcccagcc ggccatggcc caggtccagc tkcagcaatc tgg       53

<210> SEQ ID NO 41
<211> LENGTH: 53
<212> TYPE: DNA
<213> ORGANISM: Artificial Sequence
<220> FEATURE:

<223> OTHER INFORMATION: Primers for ScFv and Fab library generation
      (Table I)- MVH7

<400> SEQUENCE: 41
cctttctatg cggcccagcc ggccatggcc cagstbcagc tgcagcagtc tgg          53

<210> SEQ ID NO 42
<211> LENGTH: 55
<212> TYPE: DNA
<213> ORGANISM: Artificial Sequence
<220> FEATURE:
<223> OTHER INFORMATION: Primers for ScFv and Fab library generation
      (Table I)- MVH8

<400> SEQUENCE: 42
cctttctatg cggcccagcc ggccatggcc caggtycagc tgcagcagtc tggrc        55

<210> SEQ ID NO 43
<211> LENGTH: 53
<212> TYPE: DNA
<213> ORGANISM: Artificial Sequence
<220> FEATURE:
<223> OTHER INFORMATION: Primers for ScFv and Fab library generation
      (Table I)- MHV9

<400> SEQUENCE: 43
cctttctatg cggcccagcc ggccatggcc gaggtycagc tycagcagtc tgg          53

<210> SEQ ID NO 44
<211> LENGTH: 56
<212> TYPE: DNA
<213> ORGANISM: Artificial Sequence
<220> FEATURE:
<223> OTHER INFORMATION: Primers for ScFv and Fab library generation
      (Table I)- MHV10

<400> SEQUENCE: 44
cctttctatg cggcccagcc ggccatggcc gaggtccarc tgcaacaatc tggacc       56

<210> SEQ ID NO 45
<211> LENGTH: 54
<212> TYPE: DNA
<213> ORGANISM: Artificial Sequence
<220> FEATURE:
<223> OTHER INFORMATION: Primers for ScFv and Fab library generation
      (Table I)- MHV11

<400> SEQUENCE: 45
cctttctatg cggcccagcc ggccatggcc caggtccacg tgaagcagtc tggg         54

<210> SEQ ID NO 46
<211> LENGTH: 52
<212> TYPE: DNA
<213> ORGANISM: Artificial Sequence
<220> FEATURE:
<223> OTHER INFORMATION: Primers for ScFv and Fab library generation
      (Table I)- MHV12

<400> SEQUENCE: 46
cctttctatg cggcccagcc ggccatggcc gaggtgaass tggtggaatc tg           52

<210> SEQ ID NO 47
<211> LENGTH: 52
<212> TYPE: DNA
<213> ORGANISM: Artificial Sequence
<220> FEATURE:

<223> OTHER INFORMATION: Primers for ScFv and Fab library generation
      (Table I)- MHV13

<400> SEQUENCE: 47
cctttctatg cggcccagcc ggccatggcc gavgtgaagy tggtggagtc tg            52

<210> SEQ ID NO 48
<211> LENGTH: 55
<212> TYPE: DNA
<213> ORGANISM: Artificial Sequence
<220> FEATURE:
<223> OTHER INFORMATION: Primers for ScFv and Fab library generation
      (Table I)- MHV14

<400> SEQUENCE: 48
cctttctatg cggcccagcc ggccatggcc gaggtgcags kggtggagtc tgggg         55

<210> SEQ ID NO 49
<211> LENGTH: 54
<212> TYPE: DNA
<213> ORGANISM: Artificial Sequence
<220> FEATURE:
<223> OTHER INFORMATION: Primers for ScFv and Fab library generation
      (Table I)- MVH15

<400> SEQUENCE: 49
cctttctatg cggcccagcc ggccatggcc gakgtgcamc tggtgcagtc tggg          54

<210> SEQ ID NO 50
<211> LENGTH: 53
<212> TYPE: DNA
<213> ORGANISM: Artificial Sequence
<220> FEATURE:
<223> OTHER INFORMATION: Primers for ScFv and Fab library generation
      (Table I)- MVH16

<400> SEQUENCE: 50
cctttctatg cggcccagcc ggccatggcc gaggtgaagc tgatggartc tgg           53

<210> SEQ ID NO 51
<211> LENGTH: 55
<212> TYPE: DNA
<213> ORGANISM: Artificial Sequence
<220> FEATURE:
<223> OTHER INFORMATION: Primers for ScFv and Fab library generation
      (Table I)- MVH17

<400> SEQUENCE: 51
cctttctatg cggcccagcc ggccatggcc gaggtgcarc ttgttgagtc tggtg         55

<210> SEQ ID NO 52
<211> LENGTH: 54
<212> TYPE: DNA
<213> ORGANISM: Artificial Sequence
<220> FEATURE:
<223> OTHER INFORMATION: Primers for ScFv and Fab library generation
      (Table I)- MVH18

<400> SEQUENCE: 52
cctttctatg cggcccagcc ggccatggcc gargtraagc ttctcgagtc tgga          54

<210> SEQ ID NO 53
<211> LENGTH: 53
<212> TYPE: DNA
<213> ORGANISM: Artificial Sequence
<220> FEATURE:

<223> OTHER INFORMATION: Primers for ScFv and Fab library generation
      (Table I)0 MVH19

<400> SEQUENCE: 53
cctttctatg cggcccagcc ggccatggcc gaagtgaars ttgaggagtc tgg        53

<210> SEQ ID NO 54
<211> LENGTH: 54
<212> TYPE: DNA
<213> ORGANISM: Artificial Sequence
<220> FEATURE:
<223> OTHER INFORMATION: Primers for ScFv and Fab library generation
      (Table I)- MVH20

<400> SEQUENCE: 54
cctttctatg cggcccagcc ggccatggcc gaagtgatgc tggtggagtc tggg       54

<210> SEQ ID NO 55
<211> LENGTH: 55
<212> TYPE: DNA
<213> ORGANISM: Artificial Sequence
<220> FEATURE:
<223> OTHER INFORMATION: Primers for ScFv and Fab library generation
      (Table I)- MVH21

<400> SEQUENCE: 55
cctttctatg cggcccagcc ggccatggcc caggttactc traaagwgts tggcc      55

<210> SEQ ID NO 56
<211> LENGTH: 53
<212> TYPE: DNA
<213> ORGANISM: Artificial Sequence
<220> FEATURE:
<223> OTHER INFORMATION: Primers for ScFv and Fab library generation
      (Table I)- MVH22

<400> SEQUENCE: 56
cctttctatg cggcccagcc ggccatggcc caggtccaac tvcagcarcc tgg        53

<210> SEQ ID NO 57
<211> LENGTH: 52
<212> TYPE: DNA
<213> ORGANISM: Artificial Sequence
<220> FEATURE:
<223> OTHER INFORMATION: Primers for ScFv and Fab library generation
      (Table I)- MVH23

<400> SEQUENCE: 57
cctttctatg cggcccagcc ggccatggcc caggtycarc tgcagcagtc tg         52

<210> SEQ ID NO 58
<211> LENGTH: 53
<212> TYPE: DNA
<213> ORGANISM: Artificial Sequence
<220> FEATURE:
<223> OTHER INFORMATION: Primers for ScFv and Fab library generation
      (Table I)-MVH24

<400> SEQUENCE: 58
cctttctatg cggcccagcc ggccatggcc gatgtgaact tggaagtgtc tgg        53

<210> SEQ ID NO 59
<211> LENGTH: 53
<212> TYPE: DNA
<213> ORGANISM: Artificial Sequence
<220> FEATURE:

```
<223> OTHER INFORMATION: Primers for ScFv and Fab library generation
      (Table I)- MVH25

<400> SEQUENCE: 59
cctttctatg cggcccagcc ggccatggcc gaggtgaagg tcatcgagtc tgg      53

<210> SEQ ID NO 60
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK1

<400> SEQUENCE: 60
ttactccggt ccgcggacat tgttctcacc cagtctcc                        38

<210> SEQ ID NO 61
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK2

<400> SEQUENCE: 61
ttactccggt ccgcggacat tgtgctsacc cagtctcc                        38

<210> SEQ ID NO 62
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK3

<400> SEQUENCE: 62
ttactccggt ccgcggacat tgtgatgact cagtctcc                        38

<210> SEQ ID NO 63
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)MVK4

<400> SEQUENCE: 63
ttactccggt ccgcggacat tgtgctmact cagtctcc                        38

<210> SEQ ID NO 64
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK5

<400> SEQUENCE: 64
ttactccggt ccgcggacat tgtgytraca cagtctcc                        38

<210> SEQ ID NO 65
<211> LENGTH: 38
<212> TYPE: DNA
<213> ORGANISM: Artificial Sequence
<220> FEATURE:
```

```
<223> OTHER INFORMATION: Primers for ScFv and Fab library generation
      (Table I)-MVK6

<400> SEQUENCE: 65
ttactccggt ccgcggacat tgtratgaca cagtctcc                                38

<210> SEQ ID NO 66
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)-MVK7

<400> SEQUENCE: 66
ttactccggt ccgcggacat tmagatracc cagtctcc                                38

<210> SEQ ID NO 67
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)-MVK8

<400> SEQUENCE: 67
ttactccggt ccgcggacat tcagatgamc cagtctcc                                38

<210> SEQ ID NO 68
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK9

<400> SEQUENCE: 68
ttactccggt ccgcggacat tcagatgacd cagtctcc                                38

<210> SEQ ID NO 69
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK10

<400> SEQUENCE: 69
ttactccggt ccgcggacat tcagatgaca cagactac                                38

<210> SEQ ID NO 70
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK11

<400> SEQUENCE: 70
ttactccggt ccgcggacat tcagatcatt cagtctcc                                38

<210> SEQ ID NO 71
<211> LENGTH: 38
<212> TYPE: DNA
<213> ORGANISM: Artificial Sequence
<220> FEATURE:
```

<223> OTHER INFORMATION: Primers for ScFv and Fab library generation
      (Table I)- MVK12

<400> SEQUENCE: 71
ttactccggt ccgcggacat tgttctcawc cagtctcc                    38

<210> SEQ ID NO 72
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK13

<400> SEQUENCE: 72
ttactccggt ccgcggacat tgttctctcc cagtctcc                    8

<210> SEQ ID NO 73
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK14

<400> SEQUENCE: 73
ttactccggt ccgcggacat tgwgctsacc caatctcc                    38

<210> SEQ ID NO 74
<211> LENGTH: 36
<212> TYPE: DNA
<213> ORGANISM: Artificial Sequence
<220> FEATURE:
<223> OTHER INFORMATION: Primers for ScFv and Fab library generation
      (Table I)- MVK15

<400> SEQUENCE: 74
ttactccggt ccgcggacat ttgatgaccc artctc                      36

<210> SEQ ID NO 75
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK16

<400> SEQUENCE: 75
ttactccggt ccgcggacat tktgatgacc caractcc                    38

<210> SEQ ID NO 76
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK17

<400> SEQUENCE: 76
ttactccggt ccgcggacat tgtgatgact caggctac                    38

<210> SEQ ID NO 77
<211> LENGTH: 38
<212> TYPE: DNA
<213> ORGANISM: Artificial Sequence
<220> FEATURE:

```
<223> OTHER INFORMATION: Primers for ScFv and Fab library generation
      (Table I)- MVK18

<400> SEQUENCE: 77
ttactccggt ccgcggacat tgtgatgacb caggctgc                          38

<210> SEQ ID NO 78
<211> LENGTH: 37
<212> TYPE: DNA
<213> ORGANISM: Artificial Sequence
<220> FEATURE:
<223> OTHER INFORMATION: Primers for ScFv and Fab library generation
      (Table I)- MVK19

<400> SEQUENCE: 78
ttactccggt ccgcggacat tgtgataacy caggatg                           37

<210> SEQ ID NO 79
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK20

<400> SEQUENCE: 79
ttactccggt ccgcggacat tgtgatgacc cagtttcg                          38

<210> SEQ ID NO 80
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK21

<400> SEQUENCE: 80
ttactccggt ccgcggacat tgtgatgaca caacctgc                          38

<210> SEQ ID NO 81
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK22

<400> SEQUENCE: 81
ttactccggt ccgcggacat tttgctgact cagtctcc                          38

<210> SEQ ID NO 82
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK23

<400> SEQUENCE: 82
ttactccggt ccgcggacat tttgctgact cagtctcc                          38

<210> SEQ ID NO 83
<211> LENGTH: 38
<212> TYPE: DNA
<213> ORGANISM: Artificial Sequence
<220> FEATURE:
```

-continued

```
<223> OTHER INFORMATION: Primers for ScFv and Fab library generation
      (Table I)- MVK24

<400> SEQUENCE: 83
ttactccggt ccgcggacat tgtaatgacc caatctcc                              38

<210> SEQ ID NO 84
<211> LENGTH: 38
<212> TYPE: DNA
<213> ORGANISM: Artificial Sequence
<220> FEATURE:
<223> OTHER INFORMATION: Primers for ScFv and Fab library generation
      (Table I)- MVK25

<400> SEQUENCE: 84
ttactccggt ccgcggacat tgtgatgacc cacactcc                              38
```

SCREENING OF PHAGE DISPLAYED PEPTIDES WITHOUT CLEARING OF THE CELL CULTURE

CROSS-REFERENCES TO RELATED APPLICATIONS

This application claims the benefit of U.S. Provisional Patent application Serial No. 60/209503, filed on Jun. 5, 2000, the teachings of which are herein incorporated by reference.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Phage display and related techniques have become powerful methods for the discovery of affinity binding reagents (Smith (1985) *Science* 228: 1315–1317). Linear and constrained peptides, antibody fragments (e.g., scFvs, Fvs and Fabs), as well as a number of alternative binding domains have all been displayed on phage particles, for example, via fusion to one of the phage coat proteins. Although several phage proteins (derived from gVIII, gVI, gVII and gIX) have all been used as fusion partners for display of recombinant proteins, gIII is the most widely used. Phagemids containing a phage origin of replication, an antibiotic resistance marker, and a gene encoding a binding domain/gIII fusion protein are readily constructed via conventional molecular biology techniques. Through large-scale ligation and transformation as well as recombination strategies, large libraries of $10^8$ to $10^{11}$ different recombinants are now being generated for use in affinity selection strategies (de Haard et al. (1999) *J. Biol. Chem.* 274: 18218–18230; Sblattero and Bradbury (2000) *Nat. Biotechnol.* 18: 75–80); Sheets et al. (1998) *Proc. Natl. Acad. Sci., U.S.A.* 95:6157–6162, published erratum appears in *Proc. Natl. Acad. Sci., U.S.A.* (1999) 96: 795).

Once a library of phage displaying potential binding agents is generated, individual phage with the capacity to bind to a chosen target must be isolated from an enormous excess of non-binding phage. To screen large numbers of phage to identify those that display polypeptides having a desired activity, it is desirable to develop high-throughput screening (HTS) methods. Preferably, such HTS methods would automate the phage screening process so that large numbers of phage could be screened with little human intervention. Although HTS methods are available for many types of screening, previously known phage display protocols include steps that are not readily automatable. In particular, phage display protocols require, prior to screening, separation of the phage from the host cells in which the phage are amplified.

Traditionally, overnight cultures of bacteria producing phage are centrifuged or filtered to pellet bacteria and phage supernatants are used in the screening (See generally, Kay et al., eds. (1996) *Phage display of peptides and proteins: a laboratory manual.* Academic Press Inc., San Diego Calif.). Alternatively, phage can be purified and concentrated from cleared supernatants by precipitation (e.g., with polyethylene glycol). However, these clearing methods are not readily performed by robotic systems (e.g., automated workstations). Therefore, time-consuming and expensive human intervention is required. These drawbacks are exacerbated as the numbers of samples are increased and during high-throughput screening. Therefore, a need exists for more fully automated methods for screening of phage display libraries. The present invention fulfills this and other needs.

SUMMARY OF THE INVENTION

The present invention provides methods for screening a population of replicable genetic packages (e.g., phage, eukaryotic viruses, and the like) to obtain particles that display on their surface a fusion protein that specifically binds to a target molecule. Unlike previous methods, which involve clearing a culture of cells prior to screening the methods of the present invention involve contacting a target molecule with an uncleared cell culture that contains a population of replicable genetic packages. Each replicable genetic package displays on its surface a fusion protein that has a surface-displayed replicable genetic package polypeptide and a potential binding polypeptide. The replicable genetic package that specifically bind to the target molecule form complexes containing replicable genetic packages and target molecules. In some cases, the potential binding polypeptide can be encoded by a member of a library of nucleic acid molecules. For example, the nucleic acid molecules can be cDNA molecules or recombinant products. In other cases, the potential binding polypeptide can be, for example, an antibody, or derivative of an antibody. For example, the potential binding polypeptide can be a scFv or a Fab.

The methods of the invention are useful for obtaining polypeptides that bind to essentially any molecule. For example, the target molecule can be a polypeptide, an RNA, a DNA, a small organic molecule and a carbohydrate. The target molecules can be immobilized directly or indirectly to a solid support. Solid supports such as a bead, a chip, a microtiter plate, a eukaryotic cell, or a prokaryotic cell are present in some embodiments of the invention. The solid supports of the present invention can contain a variety of materials, such as Sepharose, polystyrene, glass, silicon oxide, etc.

In some embodiments, the methods also involve obtaining replicable genetic packages that specifically bind to the target molecule. For example, the replicable genetic packages that specifically bind to the target molecule can be separated from the bacterial cells after the binding of the phage to the target molecule. For example, the uncleared cell culture can be separated from a replicable genetic package-target complex(es) using aspiration. Once the replicable genetic packages are bound to the target molecule, some embodiments of the invention can further involve eluting the replicable genetic packages from the target molecule. Also, some embodiments involve identifying the replicable genetic packages that specifically bind to the target molecule with a detection reagent.

The present invention also provides compositions containing an uncleared cell culture, which contains: (a) a population of replicable genetic packages that display on their surfaces a fusion protein that includes a surface-displayed replicable genetic package polypeptide and a potential binding polypeptide; (b) a complex that is composed of one or members of the library of replicable genetic packages that specifically bind to the target molecule; and (c) cells in which the replicable genetic packages were amplified.

BRIEF DESCRIPTION OF THE DRAWINGS

FIG. 1A depicts representative results from the HP6054 scFv-phage, and FIG. 1B is representative of HP6054 Fab-phage.

DESCRIPTION OF THE SPECIFIC EMBODIMENTS

Definitions

Figure 1:
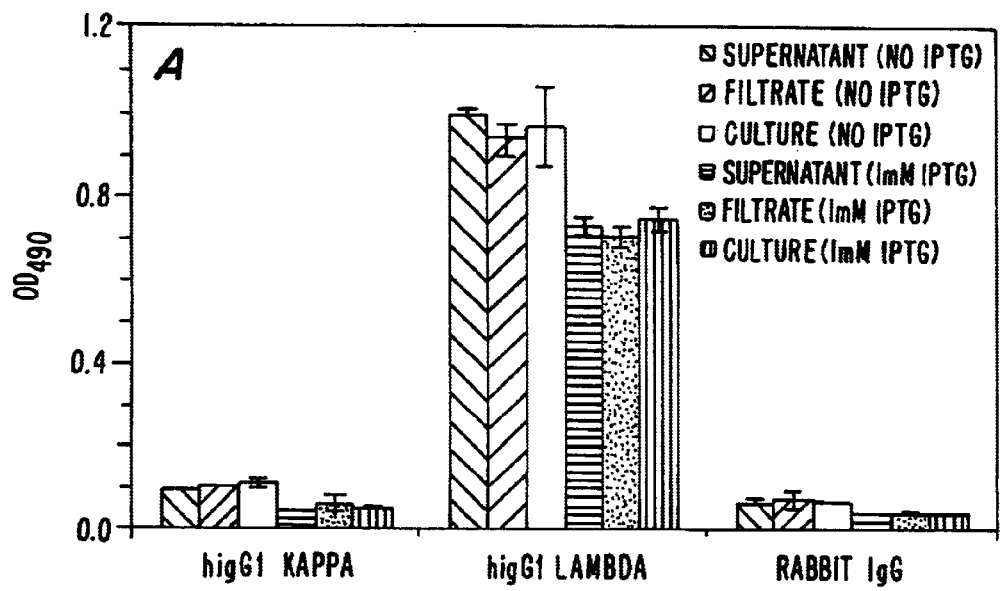
FIGS. 1A and 1B show that the binding of HP6054-scFv and HP6054-Fab phage to human lambda light chain is not affected by the presence of bacteria in the sample. Antigens were immobilized on 96-well plates (Nunc, Denmark) at 10 μg/ml. A phage ELISA was conducted using either an uncleared bacterial culture, or supernatants clarified by centrifugation or filtration. Each bar represents the mean±s.d. of duplicate samples.
Figure 1:
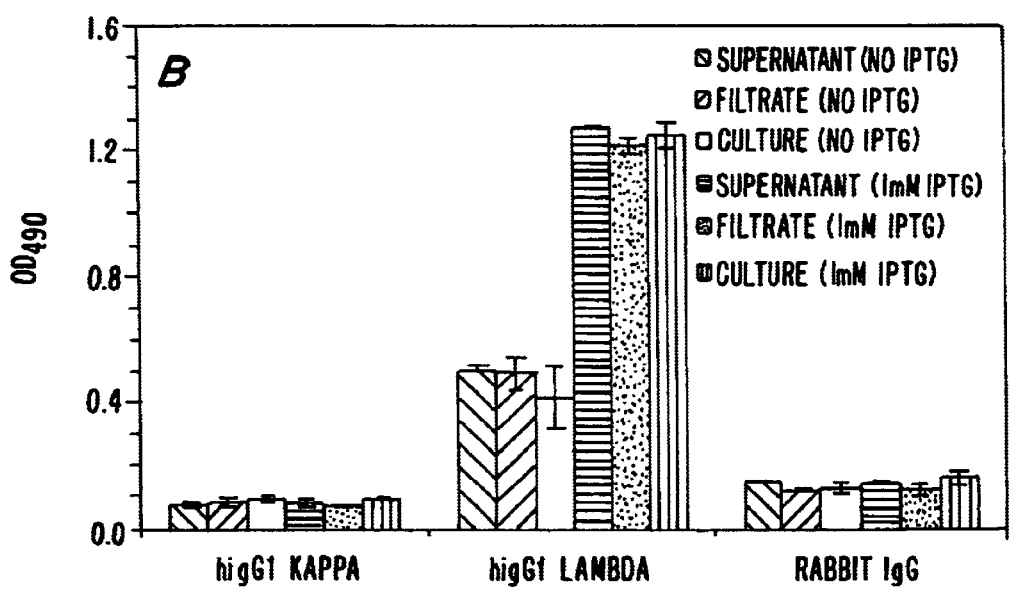

"Replicable genetic packages" include virions of bacteriophage, filamentous phage, or any other eukaryotic virus, bacterial virus or phage. The term "phage" as used herein encompasses not only bacteriophage but also other types of replicable genetic packages, except where the term is used in a context that dictates a more specific meaning.

A molecule is "display(ed) on their surface" of a replicable genetic package if at least part of the molecule is accessible to the milieu surrounding a replicable genetic package.

The phrase "specifically (or selectively) binds to" in the context of a replicable genetic package refers to a binding reaction which is determinative of the presence of a replicable genetic package binding to a target molecule(s) in the presence of a population of other proteins, biologics, and replicable genetic packages. Thus, under designated binding conditions, a specifically binding replicable genetic package will bind to a particular molecule (e.g., target molecule) and under the same designated binding conditions, native replicable genetic packages do not bind to a particular molecule in a significant amount. Typically, a replicable genetic package "specifically" binds to a target molecule when the number of replicable genetic packages displaying a potential binding polypeptide that are bound to the target molecules is at least twice the background binding observed using a native replicable genetic package as a control.

An "uncleared cell culture" is an aqueous medium containing bacterial or eukaryotic cells. Typically, the "uncleared cell culture" is a growth of bacterial or eukaryotic cells infected with one or more replicable genetic package clones.

A "target molecule" is essentially any molecule that is being used as a probe to identify molecules that will bind to the target molecule. Examples of target molecules include, without limitation, amino acids, peptides, proteins, polypeptides, carbohydrates, small organic molecules, inorganic molecules, etc.

A "surface-displayed replicable genetic package polypeptide" is a polypeptide that is, at least in part, exposed to the milieu surrounding the virion. Examples of "surface-displayed replicable genetic package polypeptides" include, without limitation, pIII and pVIII.

A "potential binding polypeptide" is a polypeptide that may possibly bind to the target molecule. A "potential binding polypeptide" can be screened for its ability to bind to a target molecule of choice.

A "replicable genetic package-target complex" is a complex in which a target molecule is bound to a replicable genetic package. The target molecule is bound to the replicable genetic package through the binding domain portion of a polypeptide displayed on the surface of a replicable genetic package.

An "antibody" can be derived from sequence of a mammal, non-mammal (e.g., birds, chickens, fish, etc.), or fully synthetic antibody sequences. A "mammal" is a member of the class Mammalia. Examples of mammals include, without limitation, humans, primates, chimpanzees, rodents, mice, rats, rabbits, sheep, and cows. The term "antibody" also refers to fragments and substitutes for antibodies such as $F(ab')_2$, Fab', and Fab fragments. Additionally the "antibodies" can be single chain antibodies known as ScFv fragments, which are obtained by recombinantly fusing the variable regions of the light and heavy chains of the antigen binding fragment of interest.

I. Introduction

The present invention provides methods and compositions for screening replicable genetic package particles (e.g., phage, viruses, etc.) that display polypeptides for their ability to bind to a target molecule. Traditionally, such screening methods required clearing the host cells or bacteria from an uncleared cell culture and/or isolating a replicable genetic package stock before incubation with the target molecule. The methods of the present invention, however, do not require these procedures. Therefore, the invention provides significant advantages over previously available methods for screening phage and other particles, particularly when used in a high-throughput format.

Briefly, methods of the invention involve infecting bacteria or other suitable host cells with phage particles (or incubating cells that are transfected with a phagemid expression vector with helper phage) to generate an uncleared cell culture that contains a library of phage particles. This uncleared culture is then incubated with a target molecule. Phage particles that display a polypeptide that binds to the target molecule form a complex with the target molecule. After an incubation period, the bacterial or other cells used to amplify the phage can be separated from the phage particles that bind to the target molecule. The phage particles that were able to bind to the target molecule can then be further purified, characterized, amplified, and/or detected, etc. These methods and compositions will be described in more detail below.

II. Replicable Genetic package Display Libraries

The methods of the invention are useful for screening a wide variety of phage display libraries. Phage display and related techniques provides a powerful method for selecting proteins of interest from large libraries (Bass et al. (1990) *Proteins: Struct. Funct. Genet.* 8: 309; Lowman and Wells (1991) *Methods: A Companion to Methods Enz.* 3(3); 205–216. Lowman and Wells (1993) *J. Mol. Biol.* 234;564–578). Each phage or other particle displays a unique variant protein on its surface and packages the gene encoding that particular variant. For example, the libraries can be composed of homogenous or heterogenous populations of phage particles. That is, each phage in the library can display the same potential binding polypeptide, or each phage can display a different potential binding polypeptide. Potential binding polypeptides can serve as epitopes, ligands, agonists, antagonists, enzymes, etc. For example, the potential binding polypeptides can encode scFvs and Fabs.

Some recent reviews on the phage display technique include, for example, McGregor (1996) *Mol Biotechnol.* 6(2):155–62; Dunn (1996) *Curr. Opin. Biotechnol.* 7(5): 547–53; Hill et al. (1996) *Mol Microbiol* 20(4):685–92;

*Phage Display of Peptides and Proteins: A Laboratory Manual.* B K. Kay, J. Winter, J, McCafferty eds., Academic Press 1996; O'Neil et al. (1995) *Curr. Opin. Struct. Biol.* 5(4):443–9; Phizicky et al. (1995) *Microbiol. Rev.* 59(1): 94–123; Clackson et al. (1994) *Trends Biotechnol.* 12(5): 173–84; Felici et al. (1995) *Biotechnol. Annu. Rev.* 1:149–83; Burton (1995) *Immunotechnology* 1(2):87–94.) See, also, Cwirla et al., *Proc. Natl. Acad. Sci. USA* 87: 6378–6382 (1990); Devlin et al., *Science* 249: 404–406 (1990), Scott & Smith, *Science* 249: 386–388 (1990); Ladner et al., U.S. Pat. No. 5,571,698.

The methods of the invention are applicable to any of the genetic packages most frequently used for phage display libraries. These include, for example, bacteriophage, particularly filamentous phage, and especially phage M13, Fd and F1. (Webster (1996) Chapter 1, *Biology of the Filamentous Bacteriophage*, in Kay et al., eds. (1996) *Phage Display of peptides and Proteins*). Microbiological methods for growing, titering, and preparing filamentous phage particles, and phage DNA are known in the art (Rider et al. (1996) Chapter 4, *Microbiological Methods*, in Kay et al., eds. (1996)) and their genomes are very well characterized. These filamentous phage have genes which encode the various capsid proteins and are known as genes III, VI, VII, VIII, and IX (Webster et al., (1996), supra). The proteins the genes encode are known as pIII, pVI, pVII, pVIII, and pIX, respectively. The most abundant capsid protein is pVIII, which has 2700 copies on the surface of the phage. Approximately 5 copies of pIII are displayed on the phage particle.

Typically, libraries of nucleic acid molecules are ligated into a phage-display vector and introduced into bacteria to create a library of particles displaying fusion proteins that consist of a surface-displayed phage polypeptide and a potential binding polypeptide. Most work has involved inserting nucleic acid libraries encoding polypeptides to be displayed into either a gIII or gVIII expression vector in order to produce phage-displayed fusion protein(s) (See, e.g., Dower, WO 91/19818; Devlin, WO 91/18989; MacCafferty, WO 92/01047 (gene III); Huse, WO 92/06204; Kang, WO 92/18619 (gene VIII)). These fusion proteins generally included a signal sequence, usually but not necessarily, from the phage coat protein, a polypeptide to be displayed and either the gene III or gene VIII protein or a fragment thereof. Exogenous coding sequences are often inserted at or near the N-terminus of gene III or gene VIII, although other insertion sites are possible. pVIII, however, can only tolerate short inserts—about 5 to 6 amino acid residues. (Armstrong et al., (1996), supra). Larger peptides can be displayed as pVIII fusions if pVIII wild-type coat proteins are interspersed with the recombinant pVIII (Malik et al. (1996) Chapter 8, *Multiple Display of Foreign Peptide Epitopes on Filamentous Bacteriophage Virions*, in Kay et al., eds. (1996)).

A variety of vectors for displaying pIII and pVIII fusion proteins in a phage display library have been described (Armstrong et al. (1996) Chapter 3, *Vectors for Phage Display*, in Kay et al., eds. (1996); Dottavio (1996) Chapter 7, *Phagemid-Displayed Peptide Libraries*, in Kay et al., eds. (1996); (Malik et al. (1996) Chapter 8, *Multiple Display of Foreign Peptide Epitopes on Filamentous Bacteriophage Virions*, in Kay et al., eds. (1996)) and are commercially available (e.g., pCANTAB5E, Pharmacia; λSurfZap, Stratagene).

Eukaryotic replicable genetic packages such as eukaryotic viruses can also be used to display polypeptides in an analogous manner. For example, display of human heregulin fused to gp70 of Moloney murine leukemia virus has been reported by Han et al., (1995) *Proc. Nat'l. Acad. Sci. USA* 92: 9747–9751.

Alternatively, prokaryotic spores can be used as replicable genetic packages. In this case, polypeptides are displayed from the outer surface of the spore. For example, spores from *B. subtilis* have been reported to be suitable. Sequences of coat proteins of these spores are described in Donovan et al., *J. Mol. Biol.* 196: 1–10 (1987). Thus, spores can be used to display the potential binding polypeptides.

The nucleic acid libraries encoding the potential binding polypeptides can be constructed from nucleic acids from a variety of sources, including cDNA, genomic DNA, synthetic nucleotides and/or from oligomers encoding randomized peptides (see, e.g., Adey et al. (1996) Chapter 5, *Construction of Random Peptide Libraries in Bacteriophage M13*, in Kay et al., eds. (1996) for descriptions of randomized peptide libraries). Random peptide libraries have been constructed using synthetic degenerate oligonucleotides and expressed as fusions with pIII (Adey et al., (1996), supra). Also, libraries of antibody and antibody fragments (Fv, scFv and Fab) can be expressed in phage display systems with pIII (McCafferty and Johnson (1996) Chapter 6, *Construction and Screening of Antibody Display Libraries*, in Kay et al., eds. (1996)). One method of constructing an antibody phage display library involves generating nucleic acids encoding antibody fragments from the amplification of variable domain gene sequences (McCafferty and Johnson (1996), supra). The fragments can be amplified from nucleic acids isolated from antigen immunized or non-immunized sources. The nucleic acids encoding variable heavy and light chain domains are then spliced together using overlap PCR and ligated into a phage-display vector to subsequently generate the antibody phage display library (McCafferty and Johnson (1996), supra).

Molecular biological methods that can be used to isolate, manipulate, and generate the nucleic acid libraries of the present invention are well known in the art and are detailed in Sambrook et al., *Molecular Cloning, A Laboratory Manual* ($2^{nd}$ ed. 1989); Kriegler, *Gene Transfer and Expression: A Laboratory Manual* (1990); and *Current Protocols in Molecular Biology* (Ausubel et al., eds., (1994)).

Numerous other methods for constructing phage display libraries are known in the art. For example, libraries expressing fragments of a protein can be used to map the epitopes of an antibody, which can serve as the target molecule (Plessis and Jordaan (1996) Chapter 9, *Phage Libraries Displaying Random Peptides Derived from a Target Sequence*, in Kay et al., eds. (1996)). Also, once a recombinant phage has been isolated or constructed, it can be used to construct a second-generation phage-display library through DNA shuffling (Adey et al. (1996) Chapter 16, *Preparation of Second-Generation Phage Libraries*, in Kay et al., eds. (1996)).

Once the nucleic acids have been introduced into an appropriate expression vector, phage particles are obtained. The vectors are introduced into appropriate host cells and amplified. Uncleared cell cultures containing libraries of phage particles can be generated using methods well known in the art (see, e.g., Sparks et al. (1996) Chapter 13, *Screening Phage-Displayed Random Peptide Libraries*, in Kay et al., eds. (1996)). For example, libraries of phage particles displaying the potential binding polypeptides can be used to infect bacteria (e.g, *E. coli*) in order to generate an uncleared cell culture. Alternatively, a library of nucleic acid molecules encoding the potential phage binding polypeptides (e.g., phagemid vectors) can be introduced into bacteria, which are subsequently infected with a helper phage (see, e.g., Sparks et al., (1996) Ch. 13, supra). These procedures can generate a library of phage particles in an uncleared cell culture.

III. Screening Replicable Genetic Package-display Libraries

Phage display libraries are screened to obtain phage that display on their surfaces a polypeptide that has a desired activity (e.g., the ability to bind to a target molecule). Methods for screening phage-displayed libraries are known in the art (Sparks et al. (1996) Chapter 13, supra); McCafferty and Johnson (1996) Chapter 6, supra; McCafferty (1996) Chapter 15, *Phage Display: Factors Affecting Panning Efficiency*, in Kay et al., eds. (1996)). To date, however, these methods involve either clearing a cell culture (e.g., by centrifugation, filtration) or isolating the entire phage library in the culture (e.g., by precipitation, centrifugation, etc.) for subsequent screening. This represents an extra step that necessitates the expenditure of extra time and effort to transfer the container or plate containing the uncleared cell culture to another format suitable for centrifugation, filtration, etc. For example, centrifugation of uncleared cell cultures that have been transferred to or grown in a microtiter plate requires transferring the plate to a centrifuge. This requires an operator to move the plate from the bench to the centrifuge, wait for the centrifugation to take place, and then remove the cleared culture from the plate to continue with the screening. These time consuming and unnecessary steps for clarifying a bacterial culture in the screening of a phage display library can be eliminated using the methods of the present invention.

Screening involves selecting phage that display on their surface a polypeptide that has a desired biological activity. Often screening entails identifying phage whose potential binding polypeptides can bind to a target molecule. In general, enough clones or pfu should be screened to ensure an adequate representation of displayed peptides is being screened. Preferably about $10^5$–$10^6$ pfu would be screened, more preferably at least about $10^9$ pfus would be screened, still more preferably at least about $10^{11}$–$10^{12}$ pfu, would be screened. Often more than one round of screening will be necessary to identify or sufficiently enrich the phage particles of interest.

Suitable target molecules include a wide variety of molecules and include a molecule for which a practitioner desires to identify or isolate a polypeptide that will bind to the target molecule. For example, the target molecule can be an antigen where a library of phage displaying antibodies (e.g., scFv or Fab) are being screened to identify antibody sequences that bind to that particular antigen. Thus, a variety of targets (e.g., peptides, proteins, carbohydrates, nucleic acids, peptide nucleic acids, RNA, DNA, small organic molecules (i.e., carbon containing molecules of 100 kDa or less, more preferably 50 kDa or less, still more preferably 10 kDa or less), inorganic molecules, etc.) can be used to probe a phage-display library. Essentially, the target can be any substance that can serve as a ligand for the potential binding polypeptide of the phage-displayed polypeptide. If possible, a positive control for the retention of binding activity of the target for a potential binding polypeptide of interest should be included in the screening process to ensure proper conditions for identifying the phage are maintained.

The immobilization of a target or target-binding molecule to a solid support can facilitate separation of replicable genetic packages that can bind to the target molecule from the cells and unbound replicable genetic packages that are present in the uncleared cell culture. One or more species of target molecules can be immobilized directly or indirectly as an array (i.e., a two or three-dimensional arrangement of molecules) on a solid support.

Those of skill in the art will recognize a variety of methods to immobilize a target molecule to a solid support. For example, the target molecule(s) can be directly or indirectly immobilized on a solid support (see below). The target molecule can be immobilized directly to the solid support through covalent and non-covalent bonds.

Alternatively, the target molecule can be indirectly bound to the solid support by coating the solid support with a substance or molecule that can bind to the target molecule. For example, the solid support can be coated with strepavidin and the target molecule can be biotinylated (Sparks et al. (1996), supra). Thus, the biotinylated target molecules can be immobilized to the strepavidin coated solid support through the biotin-strepavidin interaction. Those of skill in the art will also recognize that immobilized metal affinity substrates can be used in the present invention to indirectly bind the target molecule to a solid support (see Ausubel et al., eds., (1994) for review of immobilized metal affinity technology). For example, solid supports containing Ni—NTA (nickel-nitrilotriacetic acid) such as Ni—NTA Agarose (Qiagen) or Ni—NTA Magnetic Agarose Beads (Qiagen) can be used to bind target molecules having an N-terminal or C-terminal stretch of poly-histidine (e.g., 6 or more histidines). Ni—NTA Magnetic Agarose Beads are beads of agarose, containing magnetic particles and nitrilotriacetic acid (NTA) groups on their surfaces. The replicable genetic package-target molecule complexes can be released from a Ni—NTA substrate by an increase in the concentration of an imidazole in the solution sufficient to disrupt the poly-histidine-Ni—NTA interaction. Other suitable methods of indirectly immobilizing target molecules include the binding of a target having a ligand binding protein moiety to a support that contains a ligand for the binding protein, e.g., maltose binding protein and amylose (New England Biolabs); an antibody with an Fc domain and protein A (Sparks et al. (1996), supra); and glutathione-S-transferase and glutathione agarose (see e.g., Ausubel et al., eds., (1994), supra).

Alternatively the target can be soluble, i.e., not immobilized on a solid support. The uncleared cell culture is then incubated with the soluble target. Any resulting replicable genetic package-target complexes can subsequently be captured on a solid support by a target-binding molecule (see, e.g., Sparks et al. (1996) Ch. 13, supra; see also, methods for indirectly binding a target molecule above).

After immobilizing the target on the solid support, non-specific binding of phage to the solid support can be decreased with agents such as non-fat dry milk or BSA (bovine serum albumin). Those of skill in the art will recognize other agents that can be used alone or in combination to decrease non-specific binding such as a non-ionic detergent (e.g., Tween-20 or Triton-X-100).

A variety of solid supports can be used in the present invention. Examples of solid supports include, without limitation, bead, microtiter plates, chips, prokaryotic and eukaryotic cells. Beads can be composed of materials such as Sepharose, agarose, polystyrene, etc. and can be paramagnetic. Microtiter plates are commercially available in a variety of formats (e.g., 96, 384 and 1536 well plates) and materials (e.g., polystyrene). Chips can be comprised of a variety of materials, layers and substrates (see, e.g, WO 00/04389). For example, substances for use solid supports can be selected from a group consisting of silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for solid supports of the present invention. In addition, many ceramics and polymers may also be used as solid supports. Polymers which may be used as solid supports include, but are not limited to, the following: polystyrene; poly(tetra) fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyatkenesulfone (PAS); polypropylene; polyethylene; polyhydroxyethylmethacrylate (HEMA); polydimethylsiloxane; polyacrylamide; polyimide; and block-copolymers. The solid support on which the target resides may also be a combination of any of the aforementioned solid support materials. The solid support can also be comprised of a eukaryotic or prokaryotic cell.

IV. Separating the Replicable Genetic Package-target Complex(es) from the Uncleared Cell Culture If a population of phage or other particles include members that can specifically bind to a target molecule, those particles will bind to, and form a complex with, the target molecule. It is often desirable to remove the unbound components of the uncleared cell culture from complex (for example, removing the phage particles that do not specifically bind to the target molecule, the cells, and other components of the uncleared cell culture can be removed). In cases where the target is immobilized, directly or indirectly, on a solid support, the uncleared culture can be separated from the replicable genetic package-target complex using variety of separation methods known in the art. There are many separation methods known in the art (e.g., filtering, sedimenting, centrifuging, decanting, precipitation, etc.) that can be used or adapted for use in the present invention. For example, the where the target is immobilized on a microtiter plate, the uncleared cell culture can be aspirated from the well, leaving behind those replicable genetic packages that are bound to the immobilized target. Alternatively, the target can be immobilized on a bead and the uncleared cell culture can be passed through a filter with a pore size smaller than the bead, but larger than a bacterial cell (or a eukaryotic cell when using eukaryotic host cells). Another separation method is the immobilization of a target on a paramagnetic bead, and the decantation of the uncleared cell culture leaving the replicable genetic package-target molecule complex behind bound to the paramagnetic bead held in place with a magnetic field.

If a target is used that is free in solution, any resulting replicable genetic package-target molecule complex(es) can be subsequently separated from the uncleared cell culture. For example, the replicable genetic package-target complex can be incubated in the presence of a third molecule, a target complex-binding molecule, that is immobilized on a solid support and does not disrupt the replicable genetic package-target molecule complex(es). The target complex-binding molecule can bind to either the soluble target molecule or to the replicable genetic package. This permits the replicable genetic package-target complex to bind to the target-binding molecule, thereby indirectly immobilizing the replicable genetic package-target complex. The uncleared cell culture can then be separated from the replicable genetic packages that bind specifically to the target molecule using the separation methods described above for the first category of replicable genetic package-target complexes.

In preferred embodiments, at least 70% of the cells are separated from the replicable genetic packages that are specifically bound to the target molecule, more preferably, at least 80% of the cells are separated from the replicable genetic packages that are specifically bound to the target molecule, still more preferably, at least 90% of the cells are separated from the replicable genetic packages that are specifically bound to the target molecule, yet still more preferably, substantially all of the bacterial cells are separated from the replicable genetic packages that are specifically bound to the target molecule.

It is sometimes desirable to wash the replicable genetic package-target complex. The wash can remove undesirable components of the cell cultures from the specifically bound replicable genetic packages. The wash can remove cells, non-specifically bound replicable genetic packages, etc. Often, a wash buffer is used. The wash buffer can contain a detergent, or other agents, and compositions that are compatible with replicable genetic package-target binding to increase the stringency of the screening process. For example, a wash buffer that can be used in the present invention is a solution of Tris buffered saline with 0.05% Tween-20, pH 7.4 (TBST).

For some applications, it is desirable to elute the replicable genetic packages that specifically bind to the target molecule. The replicable genetic packages can then be used for, for example, further rounds of screening, amplification, detection, or characterization (e.g., nucleic acid sequencing). Elution can be accomplished using a variety of methods known in the art. The replicable genetic packages can be eluted using pH changes, protein denaturants, or EGTA/EDTA if a metal ion is necessary for replicable genetic package-target interaction (See e.g., Sparks et al. (1996) Ch. 13, supra for elution techniques using phage-display). For example, the replicable genetic packages can be eluted using an acidic buffer (e.g., glycine-HCl, pH 2) (see, e.g., Sparks et al. (1996) Ch. 13, supra). The eluate can then be removed and neutralized with the addition of a second buffer (e.g., $NaPO_4$ buffer pH 7.5) (see, e.g., Sparks et al. (1996) Ch. 13, supra). Alternatively, natural or synthetic ligands that interrupt the replicable genetic package-target complex can be used to elute the replicable genetic package from the target (Sparks et al. (1996) Ch. 13, supra).

If desired, the replicable genetic package(s) can be amplified in order to increase the number of replicable genetic package, thus potentially increasing the chance that enough of the replicable genetic package(s) will be present in the next round for isolation, identification, or detection, etc. Methods for amplifying replicable genetic packages in solid and liquid culture are known in the art (see, e.g., Sparks (1996), Ch. 13, supra, and Rider et al. (1996) Ch. 4, supra, for methods of amplifying filamentous bacteriophage).

Those of skill in the art will recognize that screening methods of the present invention can be optimized. Furthermore, skilled artisans will recognize methods of optimizing to determine the effectiveness of steps and to increase the chances of identifying the replicable genetic package of interest. For example, the inclusion of positive and negative controls in the screening process can facilitate the trouble-shooting and/or optimization of a screening process.

V. Detection and Characterization of Replicable Genetic Packages

Another aspect of the present invention is that the presence of cells and other components of an uncleared culture do not interfere with the detection of particles that specifically bind to a target molecule. Accordingly, some methods of the present invention involve contacting the particle-target molecule complex with a detection reagent prior to removing the cells and/or other components of the uncleared cell culture.

The presence of replicable genetic packages that bind to a target molecule can be detected using a variety of materials and methods known to those of skill in the art. For example, the replicable genetic package-target complexes can be incubated with a detection reagent. Typically, a detection reagent is labeled with a substance that permits the qualitative or quantitative determination of the presence or absence of the replicable genetic package-target complex. The term "labeled" refers to a composition is that is detectable, either directly or indirectly, by spectroscopic, photochemical, biochemical, immunochemical, or chemical means. For example, useful labels include radiolabels (e.g., $H^3$, $C^{13}$, $C^{14}$, $P^{32}$, $S^{35}$, $I^{125}$), fluorescent dyes, fluorophores, electron-dense reagents, enzymes and their substrates (e.g., as commonly used in enzyme-linked immunoassays, e.g., alkaline phosphatase and horse radish peroxidase), biotin-streptavidin, digoxigenin, or haptens and proteins for which antisera or monoclonal antibodies are available. The label or detectable moiety is typically bound, either covalently, through a linker or chemical bound, or through ionic, van der Waals or hydrogen bonds to the molecule to be detected.

Detection reagents can include antibodies—such as antibodies that react with the native form of the phage being used, e.g., anti-M13KO7 antibody. The antibody itself can be labeled. For example, horseradish peroxidase (HRP) can be conjugated to an anti-M13 antibody (Amersham-Pharmacia Biotech, Piscataway, N.J.). The absorbance of the reaction produce of HRP and o-Phenylenediamine Dihydrochloride (OPD; Sigma, St. Louis Mo.) can be monitored with a 490 nm filter (Biorad, Hercules Calif.) after stopping the reaction with acid.

The detection of the replicable genetic package-target complex on the chip could be analyzed using a physical spectroscopy method, such as mass spectroscopy or surface plasmon resonance (U.S. Pat. No. 5,641,640). Surface plasmon resonance has been used to detect phage-displayed antibody-target interactions (de Haard et al., (1999)). Chips and surface plasmon resonance instruments are commercially available (e.g., BIACORE, Uppsala, Sweden) for the detection of analytes.

Fluorescence polarization could also be employed by modifying the target molecule with an appropriate fluorescence label or fluorophore (Burke et al. (1996) Chapter 18, *Measurement of Peptide Binding Affinities Using Fluorescence Polarization*, in Kay et al., eds. (1996)).

The replicable genetic package that are bound to a target can be further characterized as to the genetic or protein makeup of their potential binding polypeptide(s). In some embodiments, the nucleic acid sequence of the potential binding polypeptide can be determined by sequencing the phagemid vector contained in a particular phage (see e.g., Masecar et al. (1996) Chapter 17, *Nonradioactive Sequencing of Random Peptide Recombinant Phage*, in Kay et al., eds. (1996)). The protein makeup of a phage could be determined using methods known in the art, such as immunological assays (e.g., Western blots), two-dimensional gels, mass spectrometry, etc.

VI. High-throughput Screening on an Automated Workstation

In the present invention, high-throughput analysis and screening of replicable genetic package-display libraries can be performed on a automated workstation (see e.g., U.S. Pat. No. 5,139,744, "Automated laboratory workstation having module identification means."). An "automated workstation" is typically a computer-controlled apparatus which can, through robotic functions, transfer, mix, and remove liquids from microtiter plates. An automated workstation can also contain a built-in plate reader, which can read the absorbance of a liquid in a microtiter well. The automated workstation can be programmed to carry out a series of mixing, transfer, and/or removal steps. The automated workstation will typically have a multi-channel pipettor which can pipette small amounts of liquid (e.g., microliter amounts) from a vessel to the well.

For example, in some embodiments of the present invention, the automated workstation can transfer uncleared cell culture(s) into a micro-titer plate. The microtiter plate can have pre-immobilized target molecule(s) already in the wells. The automated workstation can subsequently be used to remove uncleared cell cultures from the wells, wash the wells, or elute the replicable genetic packages from the immobilized target. Detection of a replicable genetic package bound to an immobilized target molecule can also be carried out using an automated workstation. The automated workstation can be used to add a detection reagent to the wells. The automated workstation, when equipped with a plate reader, can monitor the absorbance of the reaction of the detection reagent in the wells.

EXAMPLES

The following examples are offered to illustrate, but not to limit the present invention.

EXAMPLE 1
Comparison of Detection of Phage from Uncleared Bacterial Cultures and Cleared Bacterial Cultures This Example describes experiments in which alternatives to centrifugation or filtration prior to the screening of a phage-display library were explored. Phage displaying scFvs or Fabs were generated by PCR amplification of cDNA corresponding to the heavy and light chain variable regions from the HP6002, HP6025, and HP6054 hybridomas (Reimer et al. (1984) *Hybridoma* 3: 263–275) (cells obtained from ATCC Manassas, Va.; CRL-1788, CRL-1775 and CRL-1763 respectively). The regions were amplified using the primers (SEQ ID NOS: 1–84) set out in Table 1:

TABLE 1

Primer sequences for ScFv and Fab library generation
(SEQ ID NOS: 1–84

| Name | Mer | Sequence |
|---|---|---|
| MCH1-G1R | 48 | ATTGGCGCGCCTTATTAACAATCCCTGGGCACAATTTTCTTGTCCACC |
| MCH1-G2A | 44 | ATTGGCGCGCCTTATTAACAGGGCTTGATTGTGGGCCCTCTGGG |
| MCH1-G2B | 45 | ATTGGCGCGCCTTATTAACAGGGGTTGATTGTTGAAATGGGCCCG |
| MHV-Back1 | 50 | TTATTACTCGCGGCCCAGCCGGCCATGGCCGATGTGAAGCTTCAGGAGTC |

TABLE 1-continued

Primer sequences for ScFv and Fab library generation
(SEQ ID NOS: 1–84)

| Name | Mer | Sequence |
|---|---|---|
| MHV-Back2 | 50 | TTATTACTCGCGGCCCAGCCGGCCATGGCCCAGGTGCAGCTGAAGGAGTC |
| MHV-Back3 | 50 | TTATTACTCGCGGCCCAGCCGGCCATGGCCCAGGTGCAGCTGAAGCAGTC |
| MHV-Back4 | 50 | TTATTACTCGCGGCCCAGCCGGCCATGGCCCAGGTTACTCTGAAAGAGTC |
| MHV-Back5 | 51 | TTATTACTCGCGGCCCAGCCGGCCATGGCCGAGGTCCAGCTGCAACAATCT |
| MHV-Back6 | 50 | TTATTACTCGCGGCCCAGCCGGCCATGGCCGAGGTCCAGCTGCAGCAGTC |
| MHV-Back7 | 51 | TTATTACTCGCGGCCCAGCCGGCCATGGCCCAGGTCCAACTGCAGCAGCCT |
| MHV-Back8 | 50 | TTATTACTCGCGGCCCAGCCGGCCATGGCCGAGGTGAAGCTGGTGGAGTC |
| MHV-Back9 | 50 | TTATTACTCGCGGCCCAGCCGGCCATGGCCGAGGTGAAGCTGGTGGAATC |
| MHV-Back10 | 50 | TTATTACTCGCGGCCCAGCCGGCCATGGCCGATGTGAACTTGGAAGTGTC |
| MHV-For1 | 33 | ACCTGGCGCGCCTGCAGAGACAGTGACCAGAGT |
| MHV-for1b | 42 | ACCGCCTCCACCTGGCGCGCCTGCAGAGACAGTGACCAGAGT |
| MHV-For2 | 33 | ACCTGGCGCGCCTGAGGAGACTGTGAGAGTGGT |
| MHV-for2b | 42 | ACCGCCTCCACCTGGCGCGCCTGAGGAGACTGTGAGAGTGGT |
| MHV-For3 | 33 | ACCTGGCGCGCCTGAGGAGACGGTGACTGAGGT |
| MHV-for3b | 42 | ACCGCCTCCACCTGGCGCGCCTGAGGAGACGGTGACTGAGGT |
| MHV-For4 | 33 | ACCTGGCGCGCCTGAGGAGACGGTGACCGTGGT |
| MHV-for4b | 42 | ACCGCCTCCACCTGGCGCGCCTGAGGAGACGGTGACCGTGGT |
| MKV-back1 | 39 | TCTGGCGGTGGCGGATCGGATGTTTTGATGACCCAAACT |
| MKV-Back2 | 39 | TCTGGCGGTGGCGGATCGGATATTGTGATGACGCAGGCT |
| MKV-Back3 | 36 | TCTGGCGGTGGCGGATCGGATGTTGTGATAACCCAG |
| MKV-Back4 | 39 | TCTGGCGGTGGCGGATCGGACATTGTGCTGACCCAATCT |
| MKV-Back5 | 39 | TCTGGCGGTGGCGGATCGGACATTGTGATGACCCAGTCT |
| MKV-Back6 | 39 | TCTGGCGGTGGCGGATCGGATATTGTGCTAACTCAGTCT |
| MKV-Back7 | 39 | TCTGGCGGTGGCGGATCGGATATCCAGATGACACAGACT |
| MKV-Back8 | 39 | TCTGGCGGTGGCGGATCGGACATCCAGCTGACTCAGTCT |
| MKV-Back9 | 39 | TCTGGCGGTGGCGGATCGCAAATTGTTCTCACCCAGTCT |
| MKV-For1 | 38 | GATGGTGATGTGCGGCCGCCCGTTTCAGCTCCAGCTTG |
| MKV-For2 | 40 | GATGGTGATGTGCGGCCGCCCGTTTTATTTCCAGCTTGGT |
| MKV-For3 | 39 | GATGGTGATGTGCGGCCGCCCGTTTTATTTCCAACTTTG |
| MKV-For4 | 40 | GATGGTGATGTGCGGCCGCGGATACAGTTGGTGCAGCATC |
| MVH1 | 55 | CCTTTCTATGCGGCCCAGCCGGCCATGGCCGAGGTRMAGCTTCAGGAGTCAGGAC |
| MVH2 | 55 | CCTTTCTATGCGGCCCAGCCGGCCATGGCCGAGGTSCAGCTKCAGCAGTCAGGAC |
| MVH3 | 53 | CCTTTCTATGCGGCCCAGCCGGCCATGGCCCAGGTGCAGCTGAAGSASTCAGG |
| MVH4 | 55 | CCTTTCTATGCGGCCCAGCCGGCCATGGCCGAGGTGCAGCTTCAGGAGTCSGGAC |
| MVH5 | 55 | CCTTTCTATGCGGCCCAGCCGGCCATGGCCGARGTCCAGCTGCAACAGTCYGGAC |
| MVH6 | 53 | CCTTTCTATGCGGCCCAGCCGGCCATGGCCCAGGTCCAGCTKCAGCAATCTGG |
| MVH7 | 53 | CCTTTCTATGCGGCCCAGCCGGCCATGGCCCAGSTBCAGCTGCAGCAGTCTGG |

TABLE 1-continued

Primer sequences for ScFv and Fab library generation
(SEQ ID NOS: 1—84)

| Name | Mer | Sequence |
|------|-----|----------|
| MVH8 | 55 | CCTTTCTATGCGGCCCAGCCGGCCATGGCCAGGTYCAGCTGCAGCAGTCTGGRC |
| MVH9 | 53 | CCTTTCTATGCGGCCCAGCCGGCCATGGCCGAGGTYCAGCTYCAGCAGTCTGG |
| MVH10 | 56 | CCTTTCTATGCGGCCCAGCCGGCCATGGCCGAGGTCCARCTGCAACAATCTGGACC |
| MVH11 | 54 | CCTTTCTATGCGGCCCAGCCGGCCATGGCCCAGGTCCACGTCAAGCAGTCTGGG |
| MVH12 | 52 | CCTTTCTATGCGGCCCAGCCGGCCATGGCCGAGGTGAASSTGGTGGAATCTG |
| MVH13 | 52 | CCTTTCTATGCGGCCCAGCCGGCCATGGCCGAVGTGAAGYTGGTGGAGTCTG |
| MVH14 | 55 | CCTTTCTATGCGGCCCAGCCGGCCATGGCCGAGGTGCAGSKGGTGGAGTCTGGGG |
| MVH15 | 54 | CCTTTCTATGCGGCCCAGCCGGCCATGGCCGAKGTGCAMCTGGTGCAGTCTGGG |
| MVH16 | 53 | CCTTTCTATGCGGCCCAGCCGGCCATGGCCGAGGTGAAGCTGATGGARTCTGG |
| MVH17 | 55 | CCTTTCTATGCGGCCCAGCCGGCCATGGCCGAGGTGCARCTTGTTGAGTCTGGTG |
| MVH18 | 54 | CCTTTCTATGCGGCCCAGCCGGCCATGGCCGARGTRAAGCTTCTCGAGTCTGGA |
| MVH19 | 53 | CCTTTCTATGCGGCCCAGCCGGCCATGGCCGAGGTGAARSTTGAGGAGTCTGG |
| MVH20 | 54 | CCTTTCTATGCGGCCCAGCCGGCCATGGCCGAAGTGATGCTGGTGGAGTCTGGG |
| MVH21 | 55 | CCTTTCTATGCGGCCCAGCCGGCCATGGCCCAGGTTACTCTRAAAGWGTSTGGCC |
| MVH22 | 53 | CCTTTCTATGCGGCCCAGCCGGCCATGGCCCAGGTCCAACTVCAGCARCCTGG |
| MVH23 | 52 | CCTTTCTATGCGGCCCAGCCGGCCATGGCCCAGGTYCARCTGCAGCAGTCTG |
| MVH24 | 53 | CCTTTCTATGCGGCCCAGCCGGCCATGGCCGATGTGAACTTGGAAGTGTCTGG |
| MVH25 | 53 | CCTTTCTATGCGGCCCAGCCGGCCATGGCCGAGGTGAAGGTCATCGAGTCTGG |
| MVK1 | 38 | TTACTCCGGTCCGCGGACATTGTTCTCACCCAGTCTCC |
| MVK2 | 38 | TTACTCCGGTCCGCGGACATTGTGCTSACCCAGTCTCC |
| MVK3 | 38 | TTACTCCGGTCCGCGGACATTGTGATGACTCAGTCTCC |
| MVK4 | 38 | TTACTCCGGTCCGCGGACATTGTGCTMACTCAGTCTCC |
| MVK5 | 38 | TTACTCCGGTCCGCGGACATTGTGYTRACACAGTCTCC |
| MVK6 | 38 | TTACTCCGGTCCGCGGACATTGTRATGACACAGTCTCC |
| MVK7 | 38 | TTACTCCGGTCCGCGGACATTMAGATRACCCAGTCTCC |
| MVK8 | 38 | TTACTCCGGTCCGCGGACATTCAGATGAMCCAGTCTCC |
| MVK9 | 38 | TTACTCCGGTCCGCGGACATTCAGATGACDCAGTCTCC |
| MVK10 | 38 | TTACTCCGGTCCGCGGACATTCAGATGACACAGACTAC |
| MVK11 | 38 | TTACTCCGGTCCGCGGACATTCAGATCATTCAGTCTCC |
| MVK12 | 38 | TTACTCCGGTCCGCGGACATTGTTCTCAWCCAGTCTCC |
| MVK13 | 38 | TTACTCCGGTCCGCGGACATTGTTCTCTCCCAGTCTCC |
| MVK14 | 38 | TTACTCCGGTCCGCGGACATTGWGCTSACCCAATCTCC |
| MVK15 | 37 | TTACTCCGGTCCGCGGACATTSTGATGACCCARTCTC |
| MVK16 | 38 | TTACTCCGGTCCGCGGACATTKTGATGACCCARACTCC |
| MVK17 | 38 | TTACTCCGGTCCGCGGACATTGTGATGACTCAGGCTAC |
| MVK18 | 38 | TTACTCCGGTCCGCGGACATTGTGATGACBCAGGCTGC |
| MVK19 | 37 | TTACTCCGGTCCGCGGACATTGTGATAACYCAGGATG |

TABLE 1-continued

Primer sequences for ScFv and Fab library generation
(SEQ ID NOS: 1-84)

| Name | Mer | Sequence |
|---|---|---|
| MVK20 | 38 | TTACTCCGGTCCGCGGACATTGTGATGACCCAGTTTCG |
| MVK21 | 38 | TTACTCCGGTCCGCGGACATTGTGATGACACAACCTGC |
| MVK22 | 38 | TTACTCCGGTCCGCGGACATTTTGCTGACTCAGTCTCC |
| MVK23 | 38 | TTACTCCGGTCCGCGGACATTTTGCTGACTCAGTCTCC |
| MVK24 | 38 | TTACTCCGGTCCGCGGACATTGTAATGACCCAATCTCC |
| MVK25 | 38 | TTACTCCGGTCCGCGGACATTGTGATGACCCACACTCC |

Assembled scFv or Fab DNA sequences were digested with SfiI and NotI, subcloned into the pCANTAB5E vector (Amersham-Pharmacia Biotech, Piscataway, N.J.), and transformed into TG1 or XL1-Blue competent *E.coli*. Individual clones capable of specific binding to the target antigen were isolated by conventional methods and then used to explore alternatives to centrifugation. Single colonies were picked into 0.1 ml cultures (2×YT supplemented with 2% glucose and 100 µg/ml Ampicillin) in a deep well 96-well plate and incubated at 37° C. with shaking for 5–6 hours when cultures reached mid-log phase. Cultures received M13KO7 helper phage (~1×10$^9$ pfu in 5 µl) and were incubated for 1 hour at 37° C. with shaking. A 50 µl aliquot was removed to a duplicate deep well plate and 1 ml of media (2×YT supplemented with 100 µg/ml Ampicillin, 50 µg/ml Kanamycin with or without 1 mM IPTG) was added to wells for overnight growth at 30° C. Polystyrene plates were coated with protein antigens (hIgG1κK, hIgG1λ, or rabbit IgG) (1–10 µg/ml in 0.1 M sodium bicarbonate pH 9.6) overnight at 4° C., blocked with 3% non-fat dry milk (NFM) in Tris buffered saline with 0.05% Tween-20 (pH 7.4, TBST), and washed 3× in TBST. Aliquots of bacterial culture were removed to a separate microtiter plate, or to wells in a 96-well filtration plate (MultiScreen plates from Millipore, Bedford Mass.), a vacuum was applied slowly, and filtrate collected in a microtiter plate. The remainder of the culture in the deep well plates was centrifuged at 1,725×g (3,500 rpm in an Eppendorf 5804 equipped with an A2MTP rotor) for 30 minutes at room temperature (RT).

Aliquots (80 µl), of clarified phage supernatant, filtrate, or uncleared bacterial culture were added to the ELISA plate and mixed with 20 µl of 10% NFM/5×PBS directly in the wells. Plates were incubated without shaking for 1.5 hours at 37° C., then washed 4× with TBST (using a Wellwash 4 MK2 platewasher, Labsystems). Horseradish peroxidase (HRP)-conjugated anti-M13 antibody(Amersham-Pharmacia Biotech, Piscataway, N.J.) was diluted 1:5000 into 3% NFM/TBST and incubated in wells for 1 hour at 37° C. Following 4 washes with TBST, 100 µl of o-Phenylenediamine Dihydrochloride (OPD; Sigma, St. Louis Mo.) substrate was added to wells for approximately 5 minutes prior to stopping the reaction with 25 µl 13N HCl. Plates were read on a microplate reader with a 490 nm filter (Biorad, Hercules Calif.). Assays were performed in duplicate and repeated 2 or 3 times with similar results.

The scFv display phage derived from HP6054 bind to the human lambda light chain antigen (in association with IgG1), but not to the kappa light chain (hIgG1 Kappa) or to Rabbit IgG (FIG. 1A). Filtrate generated from the same culture yields an equivalent level of binding as observed for the supernatant. The uncleared bacterial culture demonstrated similar levels of binding to the immobilized antigen, indicating that removal of bacteria by time consuming centrifugation or costly filtration is not necessary. Furthermore, no increase in binding was observed to either of the two non-specific antigens tested, hIgG1κ and rabbit IgG.

Similar results were observed for phage displaying a Fab also derived from HP6054 (FIG. 1B). Addition of IPTG adversely affects the binding of HP6054 scFv-phage (due to reduced bacterial growth and phage production) and increases the binding of HP6054 Fab-phage (due to increased Fab:gIII fusion production). Although the level of IPTG did affect the overall binding of the phage populations, there were no significant differences in levels of binding observed when ELISA was performed directly on bacteria containing cultures, or cultures that were clarified by centrifugation or filtration.

EXAMPLE 2

Sensitivity of Phage ELISA is not Impaired by the Presence of bacteria

In some applications, assay of a polyclonal population of phage producing bacteria would be necessary, e.g, library screening. For example, following several rounds of selection, one might wish to test the population by ELISA to verify that binding members have been selected and are present in the population. To demonstrate that bacteria remaining during the ELISA would not present a problem when low levels of binding were expected, we grew independent cultures prior to mixing them at various ratios and then performed the ELISA on the mixed cultures or centrifuge-clarified culture supernatants derived from the same mixtures. A mixture of cultures from two clones was used as a model system to simulate a polyclonal culture. Growth of a polyclonal culture involves competition between individuals, which affects the yield of specific phage. However, the bias that is introduced during polyclonal growth would exist regardless of the means of analysis of that culture.

Figure 2:
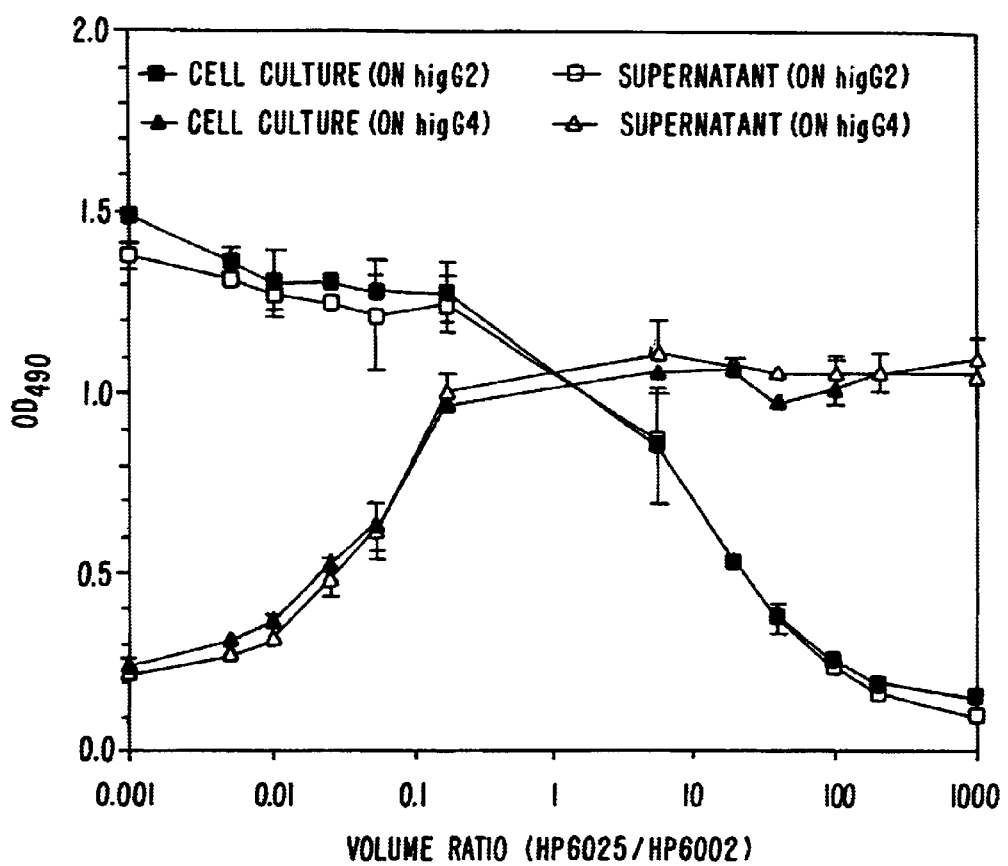
FIG. 2 shows that the sensitivity of phage ELISA is not impaired by the presence of bacteria. Overnight cultures of HP6002 scFv-phage and HP6025 scFv-phage were mixed at various ratios and then supernatants or uncleared culture was tested in the phage ELISA against hIgG2 and hIgG4 (each at 10 μg/ml). Each bar represents the mean±s.d. of duplicate samples.

*E.coli* carrying phagemid expressing scFv derived from HP6002 (recognizing hIgG2) or HP6025 (recognizing hIgG4) were grown overnight in the absence of IPTG. Cultures that attained different densities (OD$_{600}$ for HP6002 was 1.2 and 1.0, and HP6025 was 2.1 and 3.3 in two separate trials) were mixed on the basis of volume. Final volume ratios ranged from a 0.001 to 1000 of HP6025/HP6002. Aliquots of the mixed culture were compared to supernatants clarified by centrifugation in the phage ELISA. FIG. 2 demonstrates that clarified phage supernatant and bacterial culture do not exhibit significant differences in binding at any of the ratios tested. Therefore, sensitivity of the ELISA does not appear to be compromised by the presence of bacteria during the binding of the phage an immobilized antigen.

Our results demonstrate the phage ELISAs can be performed directly on bacterial culture and that there is no need to clarify by centrifugation or filtration. We have successfully used culture from scFv (5 different antibodies) and Fab (2 different antibodies) display-phage in our ELISA.

Additionally, we have used this method for analysis of both peptides and proteins displayed on the major coat protein (gene VIII protein) of filamentous phage. To date, no significant differences between culture and clarified supernatant have been observed for any display agents or antigen tested by this method.

Furthermore, this procedure has worked well with two common *E.coli* strains (TG1 cells and XL1-Blue) and overnight cultures of various densities ($OD_{600}$ from 0.1 to 3.3).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for screening a population of replicable genetic packages to obtain replicable genetic packages that display on their surface a fusion protein that specifically binds to a target molecule, the method comprising:
    contacting a target molecule with an uncleared cell culture, wherein said uncleared cell culture comprises:
    (a) replicable genetic packages, each of which displays on its surface a fusion protein that comprises a surface-displayed replicable genetic package polypeptide and an exogenous polypeptide; and
    (b) cells in which the replicable genetic packages were amplified prior to contact with the target molecule;
    wherein said replicable genetic packages that specifically bind to said target molecule via said exogenous polypeptide form complexes that comprise the target molecule and the replicable genetic packages.

2. The method of claim 1, wherein said exogenous polypeptide is encoded by a member of a library of nucleic acid molecules.

3. The method of claim 2, wherein said nucleic acid molecules are cDNA molecules.

4. The method of claim 2, wherein said nucleic acid molecules are recombinant products.

5. The method of claim 1, wherein said method further comprises separating from said complexes unbound cells and/or unbound replicable genetic package that do not specifically bind to said target molecule.

6. The method of claim 5, wherein at least 70% of said unbound cells originally present in the culture are removed.

7. The method of claim 6, wherein at least 90% of said unbound cells originally present in the culture are removed.

8. The method of claim 5, wherein said unbound cells and said unbound replicable genetic packages are separated from said complexes using aspiration.

9. The method of claim 5, wherein the method further comprises eluting said replicable genetic packages that specifically bind to said complexes.

10. The method of claim 1, wherein the presence of said replicable genetic packages are specifically bound to said target molecule is assessed by contacting the complexes with a detection reagent that binds to said replicable genetic packages.

11. The method of claim 10, wherein said detection reagent comprises an antibody.

12. The method of claim 10, wherein the complexes are contacted with the detection reagent in the presence of the cells.

13. The method of claim 1, wherein the replicable genetic packages are selected from the group consisting of bacteriophage and eukaryotic viruses.

14. The method of claim 1, wherein said target molecule is immobilized on a solid support.

15. The method of claim 14, wherein said solid support is selected from the group consisting of: a bead, a chip, a microtiter plate, a prokaryotic cell and a eukaryotic cell.

16. The method of claim 1, wherein said target molecule is selected from the group consisting of: a polypeptide, a nucleic acid, an RNA, a DNA, a small organic molecule, and a carbohydrate.

17. The method of claim 1, wherein said exogenous polypeptide is an antibody or functional fragment thereof.

18. The method of claim 17, wherein said antibody is a scFv or a Fab.

19. The method of claim 1, wherein said method is performed on an automated laboratory workstation.

* * * * *